United States Patent [19]

Smithwick et al.

[11] Patent Number: 4,767,327

[45] Date of Patent: Aug. 30, 1988

[54] DENTAL PATIENT CONTROL MECHANISM

[76] Inventors: Richard J. Smithwick, Peekskill Hollow Rd., Carmel, N.Y. 10512; George Spector, 233 Broadway Rm 3815, New York, N.Y. 10007

[21] Appl. No.: 907,835

[22] Filed: Sep. 15, 1986

[51] Int. Cl.⁴ .............................................. A61C 1/02
[52] U.S. Cl. ...................................... 433/98; 433/27
[58] Field of Search ...................... 433/27, 98, 99, 100, 433/101

[56] References Cited

U.S. PATENT DOCUMENTS

| 2,648,043 | 8/1953 | Grogl et al. | 433/98 |
| 2,650,990 | 9/1953 | Woodruff | 433/98 |
| 3,757,421 | 9/1973 | Kraft | 433/98 |

FOREIGN PATENT DOCUMENTS

| 1283334 | 11/1968 | Fed. Rep. of Germany | 433/27 |
| 0550488 | 9/1956 | France | 433/98 |
| 0727515 | 4/1955 | United Kingdom | 433/98 |

OTHER PUBLICATIONS

"Latest in Dentistry", *The Evening Star*, Jun. 20, 1935.

*Primary Examiner*—Gene Mancene
*Assistant Examiner*—Adriene J. Lepiane

[57] ABSTRACT

A patient control mechanism is provided for an air conduit circuit that has a dental unit, a foot control and a compressed air source. The mechanism consists of a first valve disposed within the air conduit circuit between the dental unit and the foot control, a second valve directly connected to the first valve and a third valve disposed within the air conduit circuit between the dental unit and the second valve. A patient can manually control the third valve by sending an air signal to the second valve which operates the first valve deactivating the dental unit if pain is felt by the patient.

7 Claims, 1 Drawing Sheet

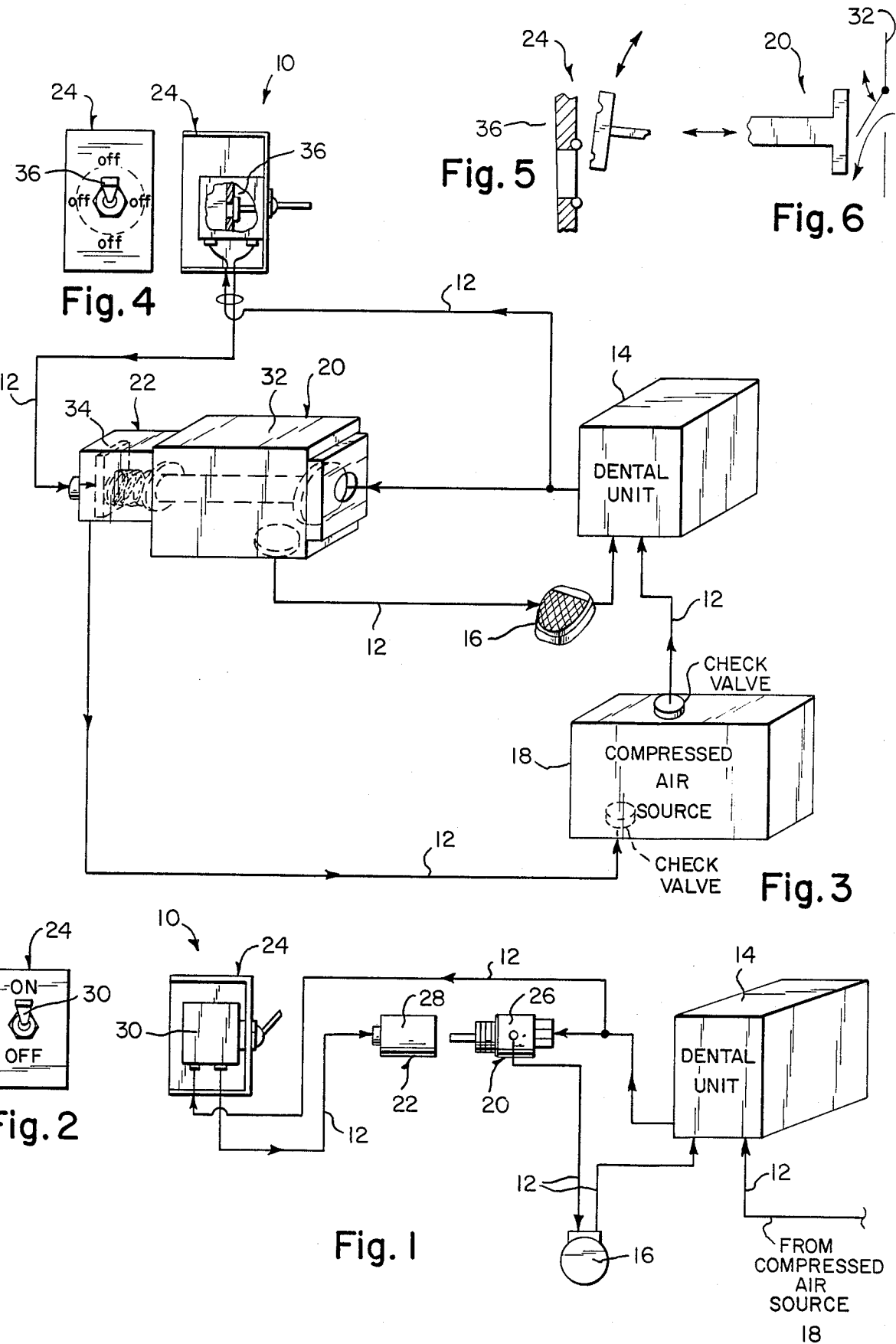

DENTAL PATIENT CONTROL MECHANISM

BACKGROUND OF THE INVENTION

The instant invention relates generally to dental equipment and more specifically it relates to a patient control mechanism for a dental unit.

Numerous dental equipment have been provided in prior art that are adapted to perform all drilling functions associated with the equipment. For example, U.S. patents numbered 3,210,846; 3,445,934 and 4,332,555 all are illustrative of such prior art. While these units may be suitable for the particular purpose to which they address, they would not be as suitable for the purposes of the present invention as heretofore described.

SUMMARY OF THE INVENTION

A primary object of the present invention is to provide a patient control mechanism for a dental unit that will overcome the shortcomings of the prior art devices.

Another object is to provide a patient control mechanism for a dental unit that will give the patient the ability to stop the dental handpiece drill, allowing the dentist to remove the handpiece drill without danger to the patient.

An additional object is to provide a patient control mechanism for a dental unit that utilizes valves, switches and other materials which are currently available on the market but when combined into a special assembly form the patient control mechanism for the dental unit.

A further object is to provide a patient control mechanism for a dental unit that is simple and easy to use.

A still further object is to provide a patient control mechanism that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a diagrammatic block diagram of a first form of the invention.

FIG. 2 is a front view of the patients switch as shown in FIG. 1 which stops the air flow to the dental unit.

FIG. 3 is a diagrammatic block diagram of a second form of the invention.

FIG. 4 is a front view of the patients switch as shown in FIG. 3 which stops the air flow to the dental unit.

FIG. 5 is an enlarged detail view of the valve which is operated by the patient to cause the dental unit to be inoperative.

FIG. 6 is a diagrammatic detail view of the plunger and inlet check valve in the air on/off valve.

DETAILED DESCRIPTION OF THE PREFERRED EMBODIMENTS

Turning now descriptively to the drawings, in which similar reference characters denote similar elements throughout the several views, FIGS. 1 and 3 illustrates a patient control mechanism 10 for an air conduit circuit 12 that has a dental unit 14, a foot control 16 and a compressed air source 18. The mechanism 10 consists of a first valve 20 disposed within the air conduit circuit 12 between the dental unit 14 and the foot control 16. A second valve 22 is directly connected to the first valve 20. A third valve 24 is disposed within the air conduit circuit 12 between the dental unit 14 and the second valve 22. A patient can manually control the third valve 24 by sending an air signal to the second valve 22 which operates the first valve 20 deactivating the dental unit 14 if pain is felt by the patient.

In FIG. 1 the first valve 20 is a normally open two way spool valve 26, the second valve 22 is a single acting, spring return miniature air pilot activator 28, while the third valve 24 is a normally closed toggle valve 30 (see FIG. 2).

In FIG. 3 the first valve 20 is a normally open two way plunger valve 32 (see FIG. 6), the second valve 22 is a single acting, tension spring impulse plate air pilot activator 34, while the third valve 24 is a normally closed ball pivot valve 36 (see FIGS. 4 and 5).

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A patient control mechanism for an air operated dental system having a main conduit having a dental unit, a foot control and a compressed air source, said mechanism being connected to said main conduit with a parallel conduit and including:
   (a) a first valve disposed within said main conduit between said dental unit and said foot control;
   (b) a valve actuator having means for actuating said first valve wherein said means is responsive to air pressure in said parallel conduit;
   (c) a third valve disposed within said parallel conduit between said dental unit and said means so that a patient can manually control said third valve to send an air signal to said means which operates said first valve closing flow in said main conduit and deactivating said dental unit if pain is felt by said patient.

2. A patient control mechanism recited in claim 1, wherein said first valve is a normally open two way spool valve.

3. A patient control mechanism as recited in claim 2, wherein said means is single acting spring return air actuated.

4. A patient control mechanism as recited in claim 3, wherein said third valve is a normally closed toggle valve.

5. A patient control mechanism as recited in claim 1, wherein said first valve is a normally open two way plunger valve.

6. A patient control mechanism as recited in claim 5, wherein said means is an air pressure single acting tension spring.

7. A patient control mechanism as recited in claim 6, wherein said third valve is a normally closed ball pivot valve.

* * * * *